United States Patent
Menon et al.

(10) Patent No.: US 10,424,400 B2
(45) Date of Patent: Sep. 24, 2019

(54) CLINICAL TRIAL INVESTIGATORS PERFORMANCE ASSESSMENT

(71) Applicant: IMS Health Incorporated, Danbury, CT (US)

(72) Inventors: Piyush Menon, San Francisco, CA (US); Suresh Kannan, Foster City, CA (US); Anil Kapu, Dublin, CA (US); Elisabeth Otto, Boulder, CO (US); Amit Ranade, Fremont, CA (US)

(73) Assignee: IQVIA INC, Parsippany, NJ (US)

( * ) Notice: Subject to any disclaimer, the term of this patent is extended or adjusted under 35 U.S.C. 154(b) by 509 days.

(21) Appl. No.: 14/554,553

(22) Filed: Nov. 26, 2014

(65) Prior Publication Data

US 2016/0147953 A1 May 26, 2016

(51) Int. Cl.
*G16H 10/20* (2018.01)
*G16H 10/60* (2018.01)
*G16H 40/20* (2018.01)

(52) U.S. Cl.
CPC ............ *G16H 10/20* (2018.01); *G16H 10/60* (2018.01); *G16H 40/20* (2018.01); *Y02A 90/22* (2018.01); *Y02A 90/26* (2018.01)

(58) Field of Classification Search
CPC .... G06F 19/327; G06F 19/322; G06F 19/363; G16H 10/20
See application file for complete search history.

(56) References Cited

U.S. PATENT DOCUMENTS

| | | | |
|---|---|---|---|
| 6,574,621 B1* | 6/2003 | Lautzenheiser | G06N 5/00 |
| 6,871,783 B2* | 3/2005 | Kaafarani | G06Q 50/22 |
| | | | 235/380 |
| 8,301,464 B1* | 10/2012 | Cave | G06Q 10/10 |
| | | | 705/2 |
| 2003/0167187 A1* | 9/2003 | Bua | G06F 19/324 |
| | | | 705/2 |
| 2005/0165623 A1* | 7/2005 | Landi | G06F 21/6254 |
| | | | 705/2 |

(Continued)

OTHER PUBLICATIONS

Otto, "SiteOptimizer Demo and Roadmap," presented at a SCOPE conference, Feb. 2014, 18 pages.

*Primary Examiner* — Jonathan Durant
*Assistant Examiner* — Chad A Newton
(74) *Attorney, Agent, or Firm* — Fish & Richardson P.C.

(57) ABSTRACT

A computer-implemented method for providing a user with a performance indicator score includes receiving a first transaction message that includes historical clinical-trial performance data from one or more processors at a clinical research organization and receiving a second transaction message with health records data with parameters indicative of insurance claims data. The received historical clinical-trial performance data and the prescription data is translated into an updated database. Related records within the updated database are identified and one or more key performance indicators included in the data at the updated database for a first physician are identified. A score for each of the one or more key performance indicators are calculated and a performance indicator score record for the first physician is generated based on the calculated scores for each of the one or more key performance indicators.

13 Claims, 10 Drawing Sheets

(56) References Cited

U.S. PATENT DOCUMENTS

| | | | |
|---|---|---|---|
| 2006/0161456 A1* | 7/2006 | Baker | G06F 19/327 |
| | | | 705/2 |
| 2006/0253773 A1* | 11/2006 | Hsieh | G06F 17/30896 |
| | | | 715/205 |
| 2008/0059486 A1* | 3/2008 | Pappas | G06F 17/30392 |
| 2011/0112416 A1* | 5/2011 | Myr | A61B 5/0006 |
| | | | 600/509 |
| 2011/0119072 A1* | 5/2011 | Lipner | G06Q 10/10 |
| | | | 705/2 |
| 2013/0110771 A1* | 5/2013 | Merriman | G06F 17/30368 |
| | | | 707/609 |

* cited by examiner

CLINICAL TRIAL INVESTIGATORS PERFORMANCE ASSESSMENT

BACKGROUND

The determination of the most efficient candidates to participate in a clinical trial can be one of the most important factors for clinical trial organizations. The assessment of investigators, that is, physicians or doctors that participate in clinical trials, is therefore essential.

SUMMARY

In one aspect, a computer-implemented method for providing a user with a performance indicator score includes receiving a first transaction message that includes historical clinical-trial performance data from one or more processors at a clinical research organization and receiving a second transaction message with health records data with parameters indicative of insurance claims data. The received historical clinical trial performance data and the health records data is translated into an updated database. Related records within the updated database are identified and one or more key performance indicators included in the data at the updated database for a first physician are identified. A score for each of the one or more key performance indicators are calculated and a performance indicator score record for the first physician is generated based on the calculated scores for each of the one or more key performance indicators.

In another aspect, receiving a second transaction message with health records data includes receiving patient data and prescriber data. In yet another aspect generating, based on the calculated scores for each of the one or more key performance indicators, a performance indicator score record for the first physician comprises calculating a weighted average of the calculated scores for each of the one or more key performance indicators. In another aspect, the weight of particular key performance indicator to the performance indicator score is based on a therapeutic area.

In another aspect, generating, based on the calculated scores for each of the one or more key performance indicators, a performance indicator score record for the first physician comprises calculating a performance indicator score based on an algorithm. In another aspect, the performance indicator score for the first physician is presented to the user. In yet another aspect, a performance indicator score record for the first physician includes generating a performance indicator score record based on a subset of the one or more key performance indicators.

In another aspect, the subset of the one or more key performance indicators used to calculate the performance indicator score record for the first physician is selected by the user. In yet another aspect, one or more key performance indicators for a second physician are identified and a score for each of the one or more key performance indicators are calculated. A performance indicator score record for the second physician is generated based on the calculated scores for each of the one or more key performance indicators.

In another aspect, the first physician and second physician are ranked by the associated performance indicator score and the ranked list is presented to the user. In another aspect, the ranked list is presented to the user based on the score for a particular key performance indicator. In yet another implementation, receiving a first transaction message that includes historical clinical-trial performance data from one or more processors at a clinical-research organization comprises receiving a data file, a stream of data or a datagram.

DETAILED DESCRIPTION

This disclosure generally describes computer-implemented methods, software, and systems for determining a performance indicator score that reflects the assessment of the performance of an investigator within clinical trials. The performance indicator score for a particular investigator, or physician, may be determined based on one or more key performance indicators (KPIs). The computer-implemented methods, systems and software integrate the historical clinical trial performance data source and the IMS data source to determine the best performing investigators. The data is visualized through the performance assessment application in the form of maps, tables, charts, and investigator scorecards.

Clinical trials are used to determine whether a new biomedical or behavioral interventions are safe, efficacious, and effective. Clinical trials may involve research studies on human subjects and are typically performed by health care providers or physicians that treat patients. The health care provider or physician may ask the patient or clinical trial subject to answer specific questions about a particular pharmaceutical product, vaccine, dietary supplements, or treatment regime. It is important that physicians participating in clinical trials are effective, and gather the required data from patients within the desired time period. It is also important that clinical trial organizations have the ability to access a quantifiable assessment of physicians. Having access to the quantifiable assessment scores of physicians make staffing a clinical trial a more reliable process.

Typically, a large percentage of all clinical trials under-enroll patients and in some instances, not even a single patient is screened. Contracting and monitoring unproductive clinical trial sites leads to a waste in time and revenue. Clinical trial organizations need to identify and enroll proven clinical trial performers, and productive sites that have access to screen a large number of patients. This will help to avoid the enrolling chronically underperforming physicians and sites into clinical trials. Identifying proven performers can also lead to enrolling physicians with experience in specialties that align with a particular clinical trial, obtaining results in a timely manner, and enrolling sites that have access to a large population of patients.

Figure 1:
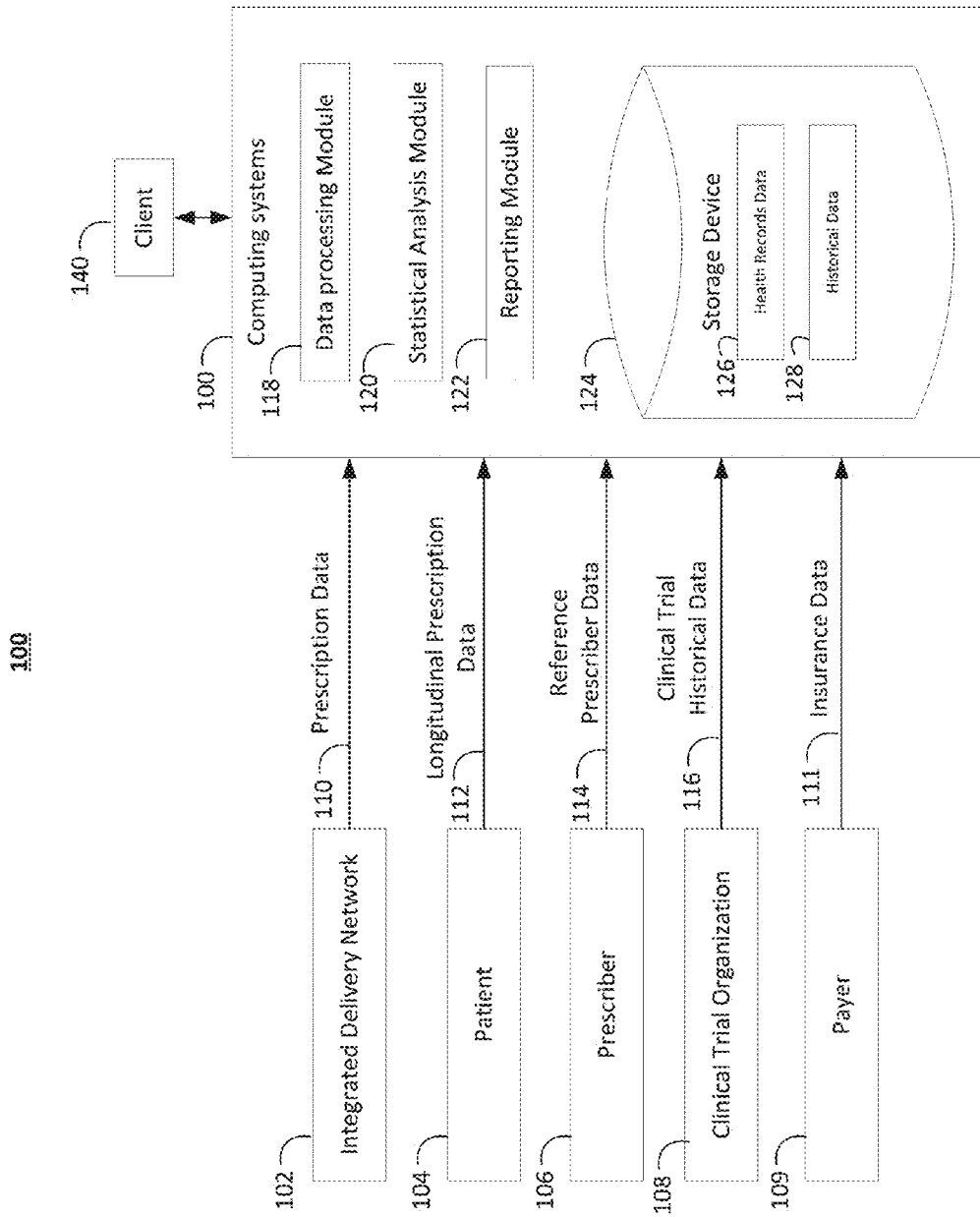
FIG. 1 illustrates an example of an analytical infrastructure system implemented in a computing system 100.

FIG. 1 illustrates an example analytical infrastructure system implemented in a computing system 100. The computing system may be implemented as a data processing apparatus that is capable of providing the functionality discussed herein, and may include any appropriate combination of processors, memory, and other hardware and software that can receive appropriate medical data and process the data as discussed below. At a high-level, the illustrated example computing system 100 receives various data from sources that are participants in the healthcare system. The sources may include IDNs 102, patient system 104, prescriber system 106, clinical trial organization 108, and payer system 109. The data may include consumption data 110, longitudinal patient data 112, reference prescriber data 114, clinical trial historical data 116, and payers insurance data 111.

FIG. 1 illustrates the process by which an analytical infrastructure is able to integrate historical data received from clinical trial organizations and IMS health data that includes insurance claims data, patient data and prescriber data. The data sources may be combined to form a universal data set that integrates the data sources. The integrated data sources may be stored as an updated database. The updated database may be an extension to the one or more databases that store the health records data and/or the clinical trial data. The updated database may be a computational database. The updated database may have the processing capability to execute extensive computations and calculations. The updated database may perform extensive calculations and computations on the health records data and the clinical trial historical data sources at the updated database high processing speeds. The updated database may be an energy efficient and time efficient database. The updated database may process large amounts of clinical trial historical data and health records data at very high speeds. The updated database may have the processing ability to allow the calculations and computations carried out on the data sources at the updated database to be quick and effective.

It is important to understand that the system may be configured to preserve patient privacy, and will not store nominative data in an aggregated database but only de-identified data.

The physician prescription data 110 may include data regarding prescriptions prescribed by physicians within an IDN. The prescription data 110 may be received directly from one or more IDNs 102 and represent data reflecting all prescriptions for pharmaceutical products issued by physicians within the one or more IDNs 102, including information about the type of prescription used to obtain the product and the payment method used to purchase the product. As noted previously, this information may be sanitized and aggregated to protect patient privacy. The prescription data may include the total revenue spent on prescriptions based on the specific drug. In some implementations, the data may be based on the total revenue spent on a specific drug in a specific geographic location. Though FIG. 1 shows the prescription data 110 being provided directly from the one or more IDNs 102 to the computing system 100, the prescription data 110 may be collected by one or more other intermediate systems and then provided to the computing system 100.

The longitudinal patient data 112 may include sanitized retail patient-level data for the one or more patient systems 104. For example, the longitudinal patient data 112 may include information about retail pharmacy-sourced prescription insurance claims, retail pharmaceutical scripts, patient electronic medical records, and/or patient profile data. Longitudinal patient data 112 includes information about aspects of care for the one or more patient systems 104. Though FIG. 1 illustrates the longitudinal patient data 112 as being received by the computing system 100 directly from one or more patient systems 104, the longitudinal patient data 112 may be collected by one or more other systems and then provided to the computing system 100 in a manner analogous to the similar approach discussed for consumption data 110. Moreover, the longitudinal patient data 112 may not originate from the one or more patient systems 104, but may rather be provided by one or more prescribers/physicians with whom the patient interacts, insurance companies to which a patient submits insurance claims, and/or retailers at which a patient purchases a pharmaceutical product. In some implementations the longitudinal patient data 112 may originate from one or more pharmaceutical companies.

The reference prescriber data 114 may include detailed data about health care providers and physicians. The reference prescriber data may include details such as the specialty of a physician, the IDN affiliation of a physician, and/or the health insurance network that the physician may be associated with. This data may be obtained through prescriptions written by the particular prescribing physician. Though FIG. 1 illustrates the reference prescriber data 114 as being received by the computing system 100 directly from one or more prescriber systems 106, the reference prescriber data 114 may be collected by one or more other systems and then provided to the computing system 100 in a manner analogous to the similar approach discussed for retail consumption data 110. Moreover, the reference prescriber data 114 may not originate from the one or more prescriber systems 106, but rather be created and/or maintained by one or more other entities (e.g., government agencies or professional medical organizations) that track information about the prescribing behavior of prescribers 106.

The clinical trial historical data 116 may include information about clinical trial that were conducted by clinical trial organizations in the past. The clinical trial historical data may include the sites and the physicians that participated in clinical trials in the past. The clinical trial historical data may include the date of past trials, and the run period of the trial. For each physician that participated in the trial, the historical data may include the number of patients screened by the physician, the length of time the physician took to enter the data collected. The clinical trial historical data may include any other data that was collected during clinical trials in the past. Though FIG. 1 illustrates the clinical trial historical data 116 as being received by the computing system 100 directly from clinical trial organization 108, the clinical trial data 116 may be collected by one or more other systems and then provided to the computing system 100 in a manner analogous to the similar approach discussed above.

The insurance data 111 may include information about insurance companies covering the cost of prescriptions. For example, the insurance data 111 may include information about how much of a prescription's cost was covered by the insurance company or by Medicaid. Though FIG. 1 illustrates the insurance data 111 as being received by the computing system 100 directly from one or more payer system 109, the insurance data 111 may be collected by one or more other systems and then provided to the computing system 100.

The various types of data just discussed, which may include prescription data 110, longitudinal prescription data 112, reference prescriber data 114, clinical trial historical data 116, and insurance data 111, are received by computing system 100 in order to derive conclusions based on the data. As noted previously, by the time the data is received by computing system 100, it should have been sanitized so that the data does not include private or confidential information that computing system 100 should not able to access.

For illustrative purposes, computing system 100 will be described as including a data processing module 118, a statistical analysis module 120, a reporting module 122, and a storage device 124. However, the computing system 100 may be any computing platform capable of performing the described functions. The computing system 100 may include one or more servers that may include hardware, software, or a combination of both for performing the described functions. Moreover, the data processing module 118, the statistical analysis module 120, and the reporting module 122 may be implemented together or separately in hardware and/or software. Though the data processing module 118, the statistical analysis module 120, and the reporting module 122 will be described as each carrying out certain functionality, the described functionality of each of these modules may be performed by one or more other modules in conjunction with or in place of the described module.

The data processing module 118 receives and processes one or more of prescription data 110, longitudinal patient data 112, reference prescriber data 114, clinical trial historical data 116, and insurance data 111. In processing the received data, the data processing module 118 may filter and/or mine the prescription data 110, longitudinal patient data 112, clinical trial historical data 114, pharmaceutical purchase data 116, and insurance data for specific information. The data processing module 118 may filter and/or mine the received prescription data 110, longitudinal patient data 112, reference prescriber data 114, clinical trial historical data 116, and insurance data 111 for specific pharmaceuticals. After processing the received prescription data 110, longitudinal patient data 112, reference prescriber data 114, clinical trial historical data 116, and insurance data 111, the data processing module 118 aggregates the processed data into patient data 126 and prescriber data 128. These groups of data may be stored in storage device 124.

In other implementations, the data processing module 118 may simply sort and store, in storage device 124, processed prescription data 110, longitudinal patient data 112, reference prescriber data 114, clinical trial historical data 116 and insurance data, the data processing module 118 for later use by other modules.

The computing systems integrate the sources of data received. The reporting module 122 prepares reports based on the integrated data sources at the computing system 100. The reports prepared by the reporting module 122 may include the performance indicator score for a particular physician. The performance indicator score may be a weighted average of score for one or more key performance indicators associated with the physician.

Additionally, in some implementations, the reports generated may be either dynamic or static. The reporting module 122 may generate a report that includes data presented in one or more static formats (e.g., a chart, a graph, or a table) without providing any mechanism for altering the format and/or manipulating the data presented in the report. In such an implementation, the data presentation is generated and saved without incorporating functionality to update the data presentation. In some implementations, the reporting module 122 provides a static report in a PDF, spreadsheet, or XML format. Such a format generally provides an understanding of the reporting module 122 as textual data or a visualization, but other forms of presenting conclusions such as audio, video, or an animation are not excluded as potential results from reporting module 122. The reporting module 122 may provide a static report in a PowerPoint format.

Additionally or alternatively, the reporting module 122 may generate a report that includes controls allowing a user to alter and/or manipulate the report itself interactively. For example, the reporting system may provide a dynamic report in the form of an HTML document that itself includes controls for filtering, manipulating, and/or ordering the data displayed in the report. Moreover, a dynamic report may include the capability of switching between numerous visual representations of the information included in the dynamic report. In some implementations, a dynamic report may provide direct access as selected by a user to some or all of the patient data 126 and prescriber data 128 prepared by the data processing module 118 and/or the statistical analysis module 120, as opposed to allowing access to only data and/or ratings included in the report itself.

One or more clients 140 may interface with the computing system 100 to request and receive reports created by the reporting system. In some implementations, the one or more clients 140 may include a web browser that provides Internet-based access to the computing system 100. Through the web browser, a user of a client 140 (e.g., a clinical trial manager, a wholesaler, a retail outlet, or a prescriber) may request a static or dynamic report from the reporting system as discussed above.

There may be any number of clients 140 associated with, or external to, the example computing system 100. While the illustrated example computing system 100 is shown in communication with one client 140, alternative implementations of the example computing system 100 may communicate with any number of clients 140 suitable to the purposes of the example computing system 100. Further, the term "client" and "user" may be used interchangeably as appropriate without departing from the scope of this disclosure. Moreover, while the client 140 is described in terms of being used by a single user, this disclosure contemplates that many users may share the use of one computer, or that one user may use multiple computers.

The illustrated client 140 is intended to encompass computing devices such as a desktop computer, laptop/notebook computer, wireless data port, smartphone, personal digital assistant (PDA), tablet computing device, one or more processors within these devices, or any other suitable processing device. For example, the client 140 may include a computer that includes an input device, such as a keypad, touch screen, or other device that can accept user information, and an output device that conveys information associated with the operation of the computing system 100. The input device may be used by client 140 to provide instructions to computing system 100 that computing system 100 can execute to provide information requested by client 140 from the various data that computing system 100 receives. The analytical infrastructure may be supported on a webpage application that a client may use to view the data received by the computing system at the analytical infrastructure.

Figure 2:
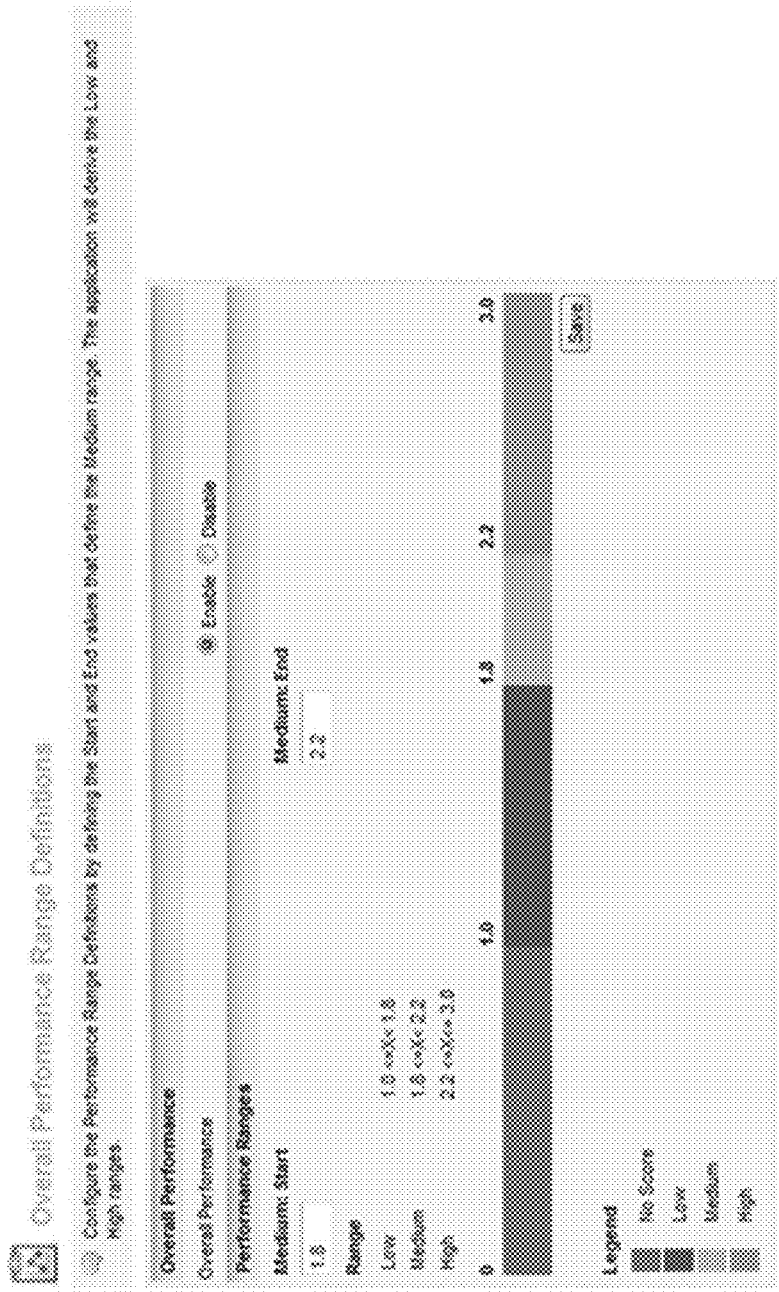
FIGS. 2-9 illustrate example user interfaces of user interaction with a webpage application of a performance indicator tool.
Figure 4:
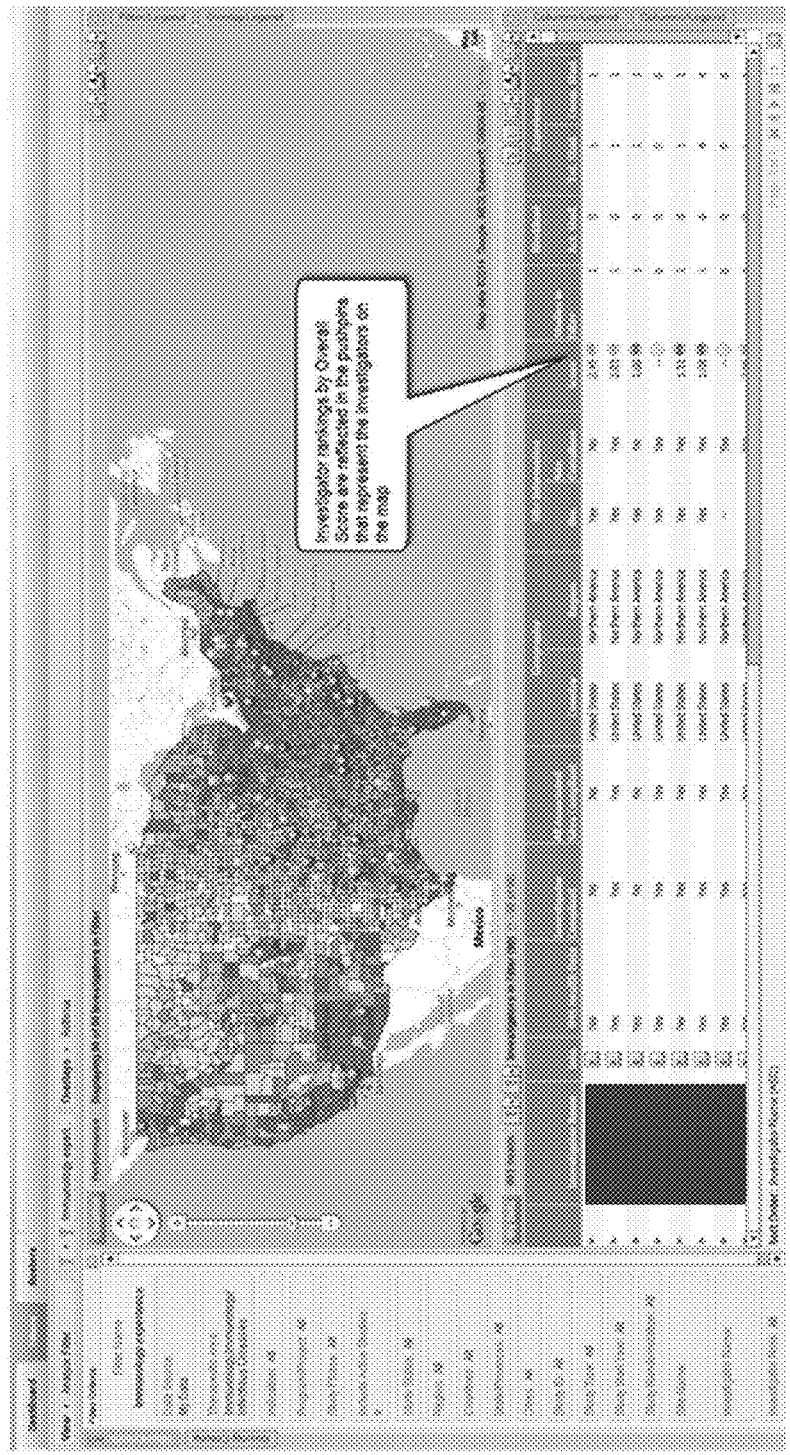

FIG. 2 illustrates an example administrative user interface for user interaction with an application of a performance indicator offering. In some implementations, interface 200 may be displayed to an internal user at IMS. The internal IMS user may act as an administrative user for the performance indicator offering. The administrative user may configure the performance indicator score range definitions. The administrative user may define the start and end values that define the medium range of the performance indicator score. The computing systems at the analytical infrastructure may then determine the low and high ranges for the performance indicator score based on the input values from the administrative user. In some implementations, the administrative user may define the values for the low, medium, and high performance indicator scores. The administrative user may define the values for the range of indicator score by any suitable means. The performance scores displayed to the end user, based on the data set of the filters selected by the user, as illustrated in FIG. 4, may be based on the performance indicator score range defined by the administrative user. For the example illustrated in FIG. 2, the administrative user may set the start value for the medium performance indicator score at 1.8 on a scale of 1 to 3, and may set the end value for the medium performance indicator score at 2.2. In some implementations, the end user may have the ability to define the performance indicator range. The performance indicator score may be based on a scale of 1 to 10, 1 to 100, or any other suitable scale.

Figure 3:
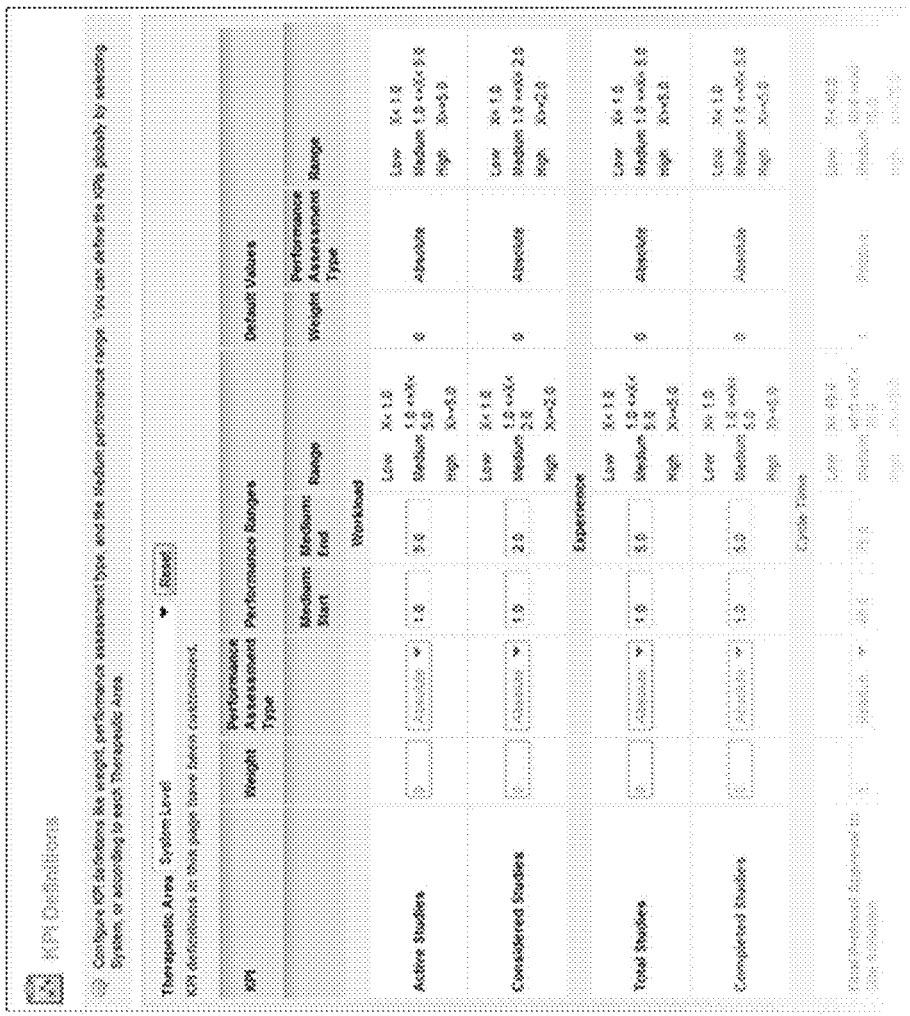

FIG. 3 illustrates an example administrative user interface for the performance indicator offering. As described above, an administrative user may be an internal user at IMS. Interface 300 may be displayed when the administrative user logs into a secure connection to the performance indicator offering. The administrative user may define the key performance indicators to determine how each key performance indicator contributes to the overall performance indicator score. The determination set by the administrator may be used across the one or more clinical trial organizations and/or pharmaceutical companies that utilize the performance indicator offering to evaluate investigators to staff on a clinical trial. In some implementations, the end user at the clinical trial organization and/or pharmaceutical company may have the ability to configure the contribution of each key performance indicator to the overall performance indicator score for an investigator. The end user at the clinical trial organization and/or pharmaceutical company may have the ability to identify which key performance indicators should be included to determine the overall performance indicator score for an investigator.

As illustrated in FIG. 3, the user may define the key performance indicators across the entire system by selecting the system level option from a drop down tab. The user may also define the key performance indicators according to a specific therapeutic area by selecting the therapeutic area from the therapeutic area drop down tab. The user interface may list the key performance indicators, the performance range associated with each key performance indicator, and the default value associated with each key performance indicator. The list of key performance indicators may include active studies, considered studies, total studies, completed studies, final protocol approval to site initiation, institutional review board approval to site initiation, site initiation to first patient screened, site initiation to last patient screened, site initiation to last patient randomized, patients randomized, percent of target randomized, screening rate, screen failure percent, randomization rate, dropout percent, data entry lag, time to resolve queries, protocol violations, regulatory audits, and queries. The key performance indicators may further include in other suitable key performance indicator that may be revealed from the data at analytical infrastructure. In some implementations, the administrative user may define the parameters for a key performance indictor based on the data set available at the analytical infrastructure. The key performance indicators may be grouped into one or more categories. The categories may include Experience, Workload, Cycle Time, Throughput, Data management, and Data Quality. The one or more key performance indicators may be grouped into any suitable category.

The Workload and Experience categories may include the active studies, considered studies, total studies and completed studies key performance indicators. These categories of key performance indicators measure the experience of investigators in terms of the number of clinical trial studies an investigator has participated in the past. The investigator experience may be gathered from the clinical trial historical data that is received by the computing systems at the analytical infrastructure. The active studies indicator identifies the number of currently active clinical trial studies that an investigator is currently participating. The data processing module at the analytical infrastructure may field and/or mine the clinical trial historical data received. The data processing module may include a study as an active study when evaluating the performance of an investigator based on administrative set criteria. The administrative user may exclude active and historical clinical trial studies data from the evaluation of the performance indicator score of an investigator. The performance data from the sites for any excluded clinical trial studies may not be included in the performance analysis. In some implementations, the end user may have the ability to determine whether data from an active clinical trial study should be included in the evaluation of the performance indicator score of an investigator.

The considered studies indicator identifies the number of unique clinical trial studies for which an investigator is being considered to participate. The data processing module may include a clinical trial study when evaluating the performance of an investigator when the investigator is included on a roster for a clinical trial study. The total studies indicator identifies the total number of clinical trial studies that an investigator has participated. In some implementations, this indicator may include clinical trials that have already been completed and clinical trials that are currently active. The completed studies indicator identifies the number of studies that an investigator has completed work.

The Cycle time category may include final protocol approval to site initiation, institutional review board approval to site initiation, site initiation to first patient screened, site initiation to last patient screened, and site initiation to last patient randomized key performance indicators. The cycle time category of key performance indicators measures how quickly an investigator was able to achieve site initiation and patient screening milestones. The final protocol approved to site initiation indicator measures the time between the date the final protocol was approved and the date the site initiated the study. The institutional review board approval to site initiation indicator measures the time between the date of the country level institutional review board approval for a clinical trial and the date the site initiated the clinical trial. The site initiation to first patient screened indicator measures the time between the site's initiation date and the date when the first patient was screened for a clinical trial study. The site initiation to last patient screen measures the time between the site's initiation date and the date when the last patient was screened at the site. The site initiation to last patient randomized indicator measures the time between the site's initiation date and the date when the last patient was randomized into the site. The time period for the key performance indicators that fall within the cycle time category may measure time in days, weeks, quarters, or months, or any other suitable time period. In some implementations, the administrative user may set the time unit used.

The Throughput category may include patients randomized, percent of target randomized, screening rate, screen failure percent, randomization rate, and dropout percent key performance indicators. The throughput category of key performance indicators are used to evaluate an investigator's ability to process numbers of patients. The patients randomized indicator may be used to show the patient volume by calculating the number of patients who were randomized by an investigator. The percent of target randomized indicator may indicate the investigator's ability to meet commitments by calculating the patients who were randomized as a percentage of the original target. The screening rate indicator may show an investigator's patient volume by calculating the average number of patients who were screened per site per unit time. The screen failure percentage may measure an investigator's ability to screen patients by calculating the average percentage of patients who failed screening out of the total number of patients screened. The randomization rate indicator shows an investigator's patient volume by calculating the average number of patients who were randomized per site, per unit time. The dropout percent shows an investigator's ability to retain patients by calculating the average percentage of patients who left a clinical trial study after being randomized.

The Data Management and Quality category of key performance indicators may include data entry lag, time to resolve queries, protocol violations, regulatory audits, and queries indicators. The data entry lag indicator may evaluate the average time between a patient visit and a data entry for the visit. The time to resolve queries indicator may measure the average time between the query and the resolution. The protocol violations indicator may measure an investigator's ability to follow the protocol for a clinical trial without incurring violations. The regulatory audits indicator may evaluate how frequently the investigator generated regulatory audits. The queries indicator may evaluate how frequently the investigator generated queries.

For each listed key performance indicator, the administrative user has the ability to configure the medium start and medium end ranges. In some implementations, the administrative user may configure the application to run using the default values. In some implementations, the end user may have the ability to configure the performance ranges for one or more of the key performance indicators.

FIG. 4 illustrates an example user interface for user interaction with an application of a performance indicator offering. The end user may be a client 140 that accesses the web-application to the computing systems 100 at the analytical infrastructure. The user may be a user at a clinical trial organization, or the user may be a representative at a pharmaceutical company that is interested in staffing a clinical trial. The end user may use the performance indicator offering to identify a list of investigators, or physicians, that are ranked based on their clinical trial performance. The end user may use the performance indicator offering to compare one or more physicians based on one or more sets of metrics. The performance indicator offering may compare the one or more physicians based on patient availability derived from health insurance claim information. Interface 400 may be displayed when a user logs into a secure connection with the performance indicator offering. The user may log into the application by providing a user specific user name and password, or any other suitable user authentication mechanism. The webpage may be specific to individual users of the application, that is, the webpage generated is specific to the user. In some implementations, the user may have the option to customize the information displayed on the web page. The performance indicator offering may enable the user to evaluate the performance of an investigator against other investigators on a worldwide, regional, and country wide comparison. The user may view an investigator's performance for a particular key performance indicator, as well as, view an investigator's performance against the performance of other investigators.

The user interface may include a list of filters. The list of filters may be displayed on the left panel of the user interface. The filters panel may include a data source filter, a therapeutic area filter, an indication filter, a program filter, a study phase filter, a region filter, a study type filter, and a study randomizer filter. In some implementations, the filter panel may include a subset of these filters, and in some implementations, the filter panel may include any other suitable filters. The end user may use a drop down selection tab to indicate which filters should be activated to generate the ranked list of investigators. For example, the end user may select what countries and/or what other geographical locations should be included in the dataset for determining the ranked list of investigators. For the example illustrated in FIG. 4, the end user selected all the states and cities of the United States to be included. The user interface illustrates a map of the selected geographical location with one or more push pins that indicate the overall scores of investigators across the selected geographical region. In some examples, a push pin may be used to identify the geographical location of the top ranked investigators based on the user selected filters. The size and color of the push pin used to identify the geographical location may be selected by the user. The user interface may also include a ranked list of investigators that reflects the data illustrated in the map. The ranked list may include details for each of the one or more investigators listed. For example, the list may include the investigator name, the geographical location of the investigator, the generated performance indicator score for the investigator, the scores for each of the one or more key performance indicators evaluated, and the experience of the investigator. In some implementations, the investigator's details may include the investigator contact information, and may include the option to add an investigator to a roster schedule. In some implementations, the user may select to rank the investigators based on one more key performance indicators scores. For example, the user may select to rank investigators based the score for both the screening rate and protocol violations key performance indicators. In another example, the user may select to rank the investigators by an overall performance indicator score and the score for screening rate.

The end user may have the ability to select a particular investigator from the ranked list to view further details about the selected investigator. In some implementations, the details may include the specialty area of the investigator, the IDN affiliations of the investigator, and the list of colleagues of the selected investigator that are affiliated with the same IDN network. In some implementations, the details may include a list of key performance indicators that were used by the computing systems at the analytical interface to generate the performance indicator score for the investigator.

Figure 5:
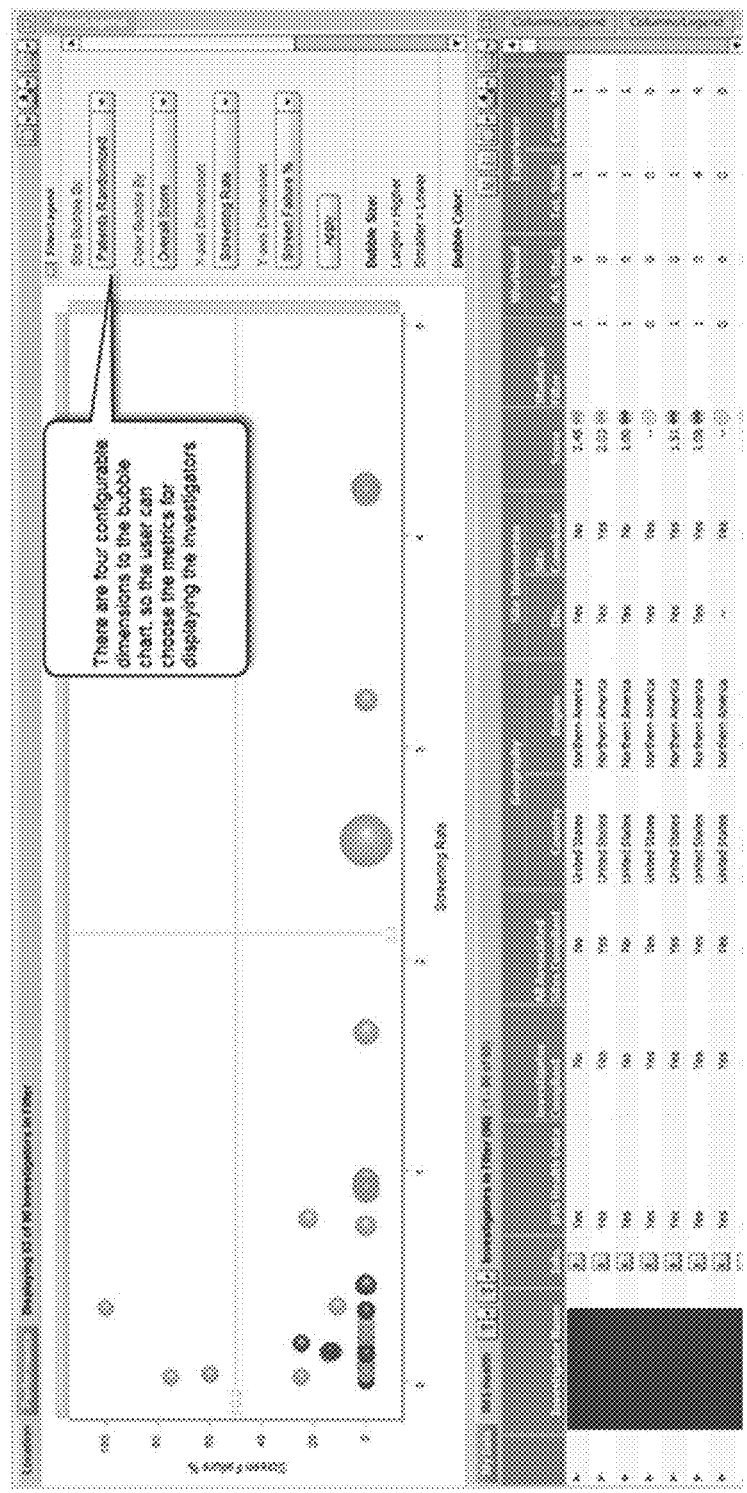

FIG. 5 illustrates an example user interface for user interaction with an application of a performance indicator offering. Interface 500 may be displayed when a user logs into a secure connection with the performance indicator application offering. The user may log into the application by providing a user specific user name and password, or any other suitable user authentication mechanism. The webpage may be specific to individual users of the application, that is, the webpage generated is specific to the user. The user interface 500 may be displayed when the user selects a performance tab on the task bar.

As illustrated in FIG. 5, the computing systems at the analytical infrastructure may display a bubble chart based on an evaluation of investigators. The results may be displayed in any suitable type of chart. In some implementations, the user interface may display the overall score determined for each investigator as a ranked list. The user may have the ability to configure the results to be displayed in a chart. As illustrated in interface 500, the user interface may include a task pane that includes one or more configurable dimensions. The user may select through drop down task bars, the x-axis dimension of the chart, the y-axis dimension of the chart, the color of the bubbles used on the chart, and the bubble size. For the example illustrated, the user selected the bubble size to indicate the number of patients randomized, the color of the bubble to indicate the overall score for an investigator, the x-axis to indicate the screen rate and the y-axis to indicate the screen failure percent. The user selected metrics are then used by the computing systems at the analytical infrastructure to generate a bubble chart. The bubble chart clearly depicts the received data for each investigator and allows the user to manipulate the data that is plotted to get a true understanding of each of the key performance indicators that were used to evaluate an investigator.

Figure 6:
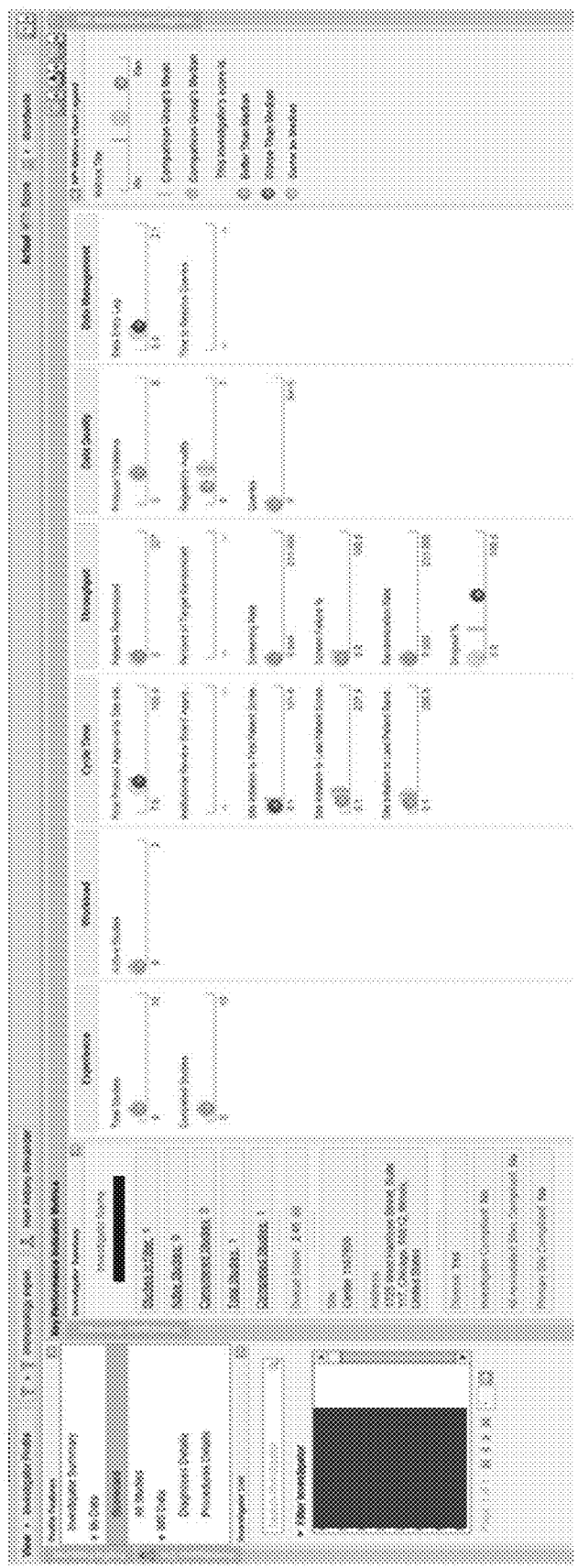

FIG. 6 illustrates an example user interface that may be displayed when a user selects an individual investigator from the ranked list of investigators. The user interface 600 displays the investigator's score card that includes the one or more metrics used to determine the overall performance indicator score for the selected investigator. The investigator score card may include the score determined for each key performance indicator used to determine the overall performance indicator score. The score card may include the investigator details such as the investigator name, address, therapeutic area, IDN affiliation, or any other suitable detail. The score card may also include the investigator performance relative to aggregate metrics for the comparison group like minimum/maximum/median/mode. In some implementations, the set of clinical trial studies used for the computation of scores for the one or more key performance indicators may be dynamically altered. For example, the data gathered from one or more clinical trial studies may be excluded from the analysis. In some implementations, the investigator performance is compared relative to all investigators across the selected geographical area. In other implementations, the investigator performance is compared relative to a worldwide group of investigators. The user may have the ability to select the comparison group using the web-based application.

Figure 7:
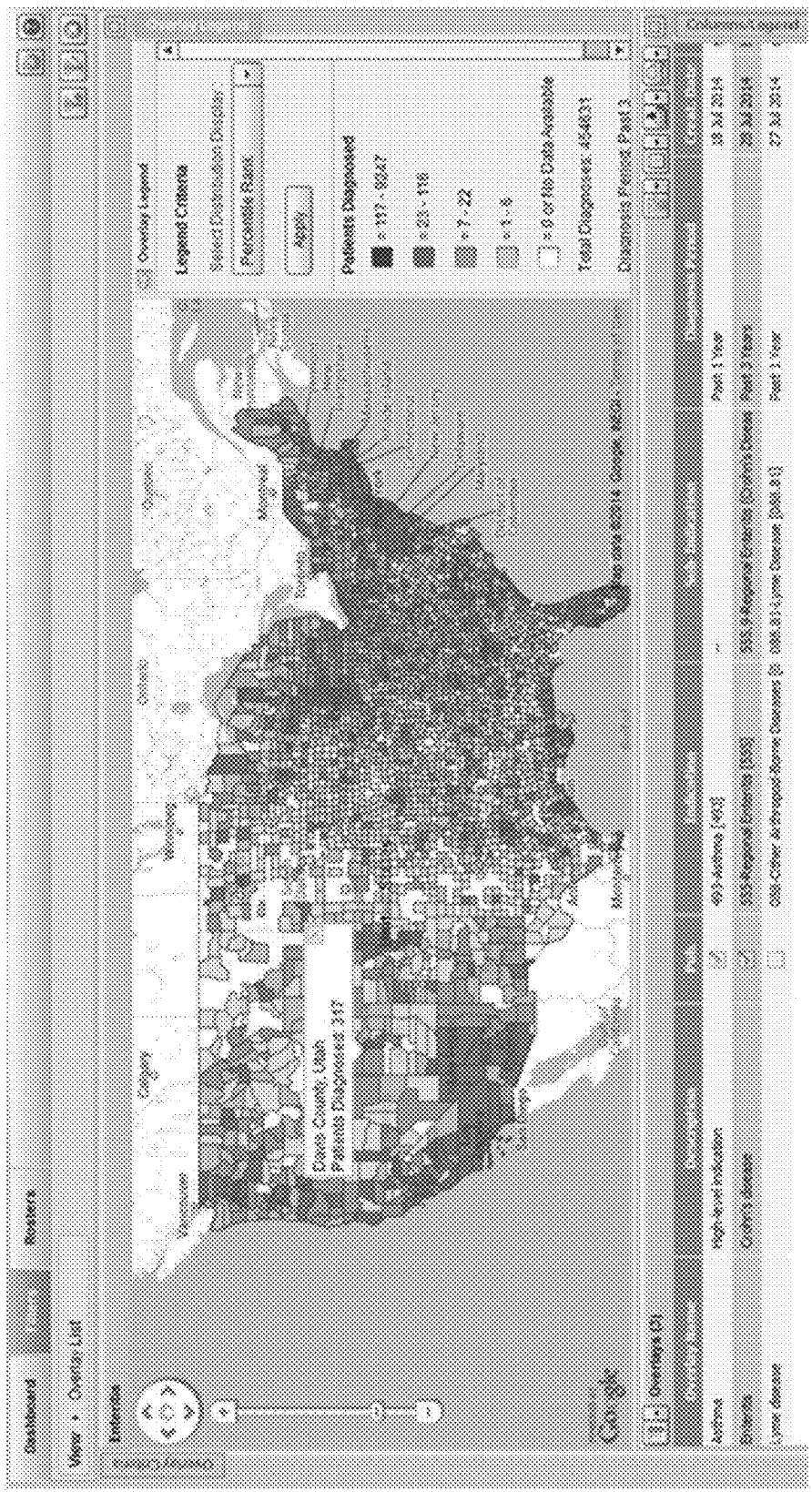

FIG. 7 illustrates a user interface 700 that may be displayed when a user of the performance indicator offering selects the overlay view. The computing systems at the analytical infrastructure may integrate the historical clinical trial data with prescription data, patient data, and insurance claims data. As illustrated in interface 700, the computing systems at the analytical infrastructure, may use the integrated data sources to produce a heat map. The heat map may display, for a selected geographical area, the patient diagnoses for a selected time frame. In some implementations, the heat map may display the patient diagnosis data for an entire country. The computing systems at the analytical infrastructure may use one or more different colors or shade of colors to represent the one or more different patient diagnoses ranges. In some implementations, the heat map may be displayed according to percentile rank. For the example illustrated, four patient ranges are used to represent the $1\text{-}25^{th}$, $26\text{-}50^{th}$, $51^{st}\text{-}75^{th}$ and $76^{th}\text{-}100^{th}$ percentiles. In some implementations, the patient ranges may represent any suitable diagnosis percentiles. The user interface may also include a list of diagnoses that a user may scroll through and select for which diagnosis the heat map should be displayed for. For the example illustrated in FIG. 7, the user selected the diagnosis Enteritis for the period of the past three years. The computing systems at the analytical infrastructure may indicate on the map, the geographical location with the highest number of patient diagnoses. The patient diagnosis information may be granular, and may display patient diagnosis data on a county by county basis.

Figure 8:
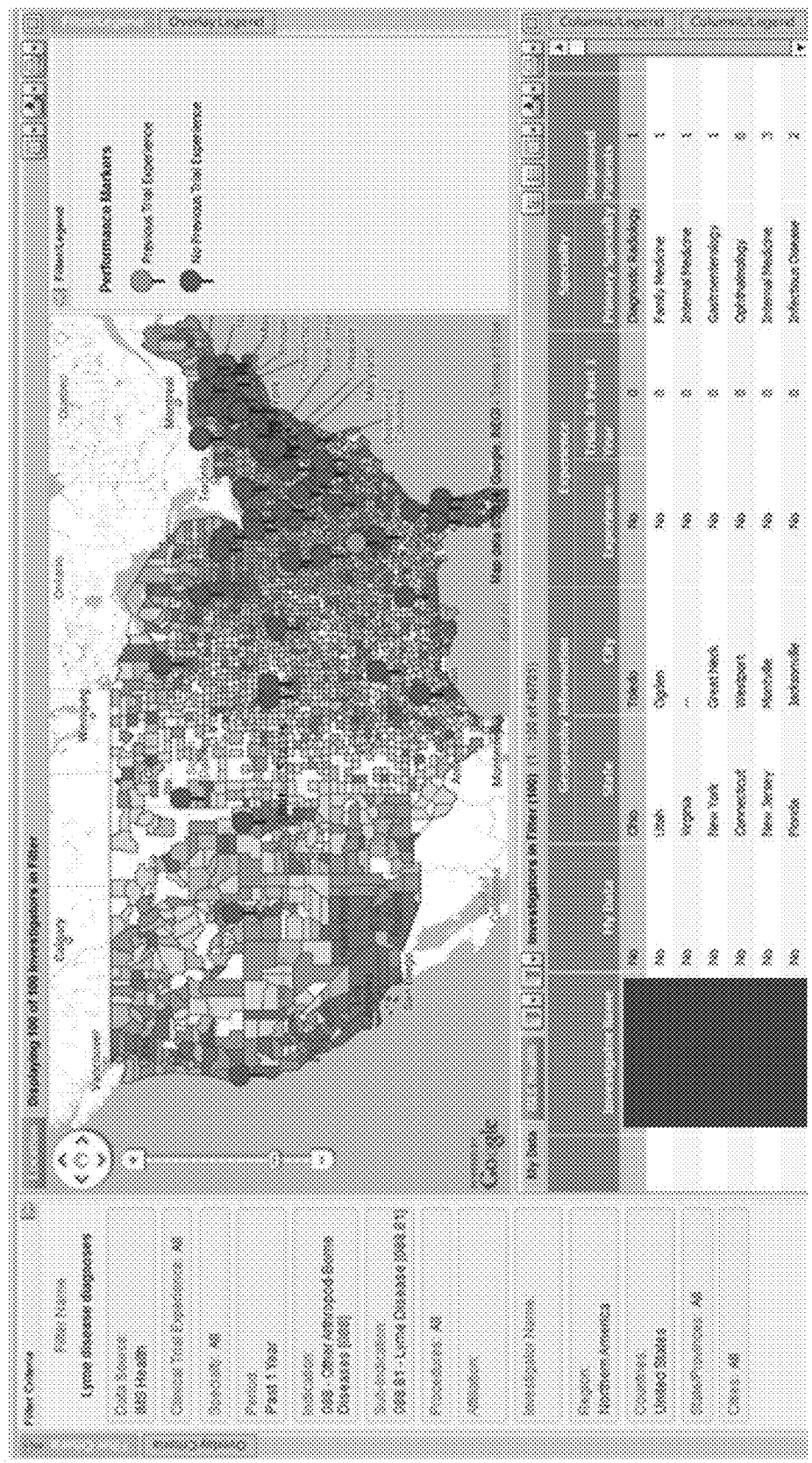

FIG. 8 illustrates an example user interface 800 that may be displayed when a user of the performance indicator offering selects to view data for a particular diagnosis within the received health records data. In some implementations, the health records data may include health insurance claims data, patient data, and prescribing data. The user may select which data set to mine to display diagnosis data. For example, the user may select to view diagnosis data from only health insurance data. The user may select an indication, a sub-indication, and a time interval for the data to be displayed. For the example illustrated, the user selected the indication "other arthropod borne diseases" and selected the sub-indication "Lyme disease." The computing systems at the analytical infrastructure may generate a map to illustrate a list of investigators that have made diagnoses of the user selected diagnosis. For the example illustrated in FIG. 8, the computing systems may generate a ranked list of investigators based on the selected diagnosis. The map illustrated may also indicate the location of the investigators on the ranked list. The geographical location of the ranked investigators may be indicated on the map with marker. The marker may also indicate the clinical trial experience of the investigator. In some implementations, the marker may indicate the investigators experience by the color of the marker. The ranked list of the investigators may be displayed below the generated map. The ranked list of investigators may list the name of the investigator, the city and or state of the investigator, the investigator specialty, the investigator clinical trial experience, and the number of patients the investigator diagnosed within the user selected time period. In some implementations, the ranked list may include the number of clinical trials the investigator participated within the last year, and an indication whether the investigator has participated in a clinical trial carried out by the clinical trial organization associated with the user.

In some implementations, the user may narrow the list of investigators by applying one or more different filters to the search criteria. For example, the user may indicate, using a filter, to have only investigators with an overall performance score over a predetermined threshold be displayed. In some implementations, the user may select to display a ranked list of investigators based on the score for a particular key performance indicator. For example, a user may select to rank the investigators based on the key performance indicator of completed studies. In some implementations, the computing systems may generate the ranked list of investigators based on a universal data set. The universal data set may include all data sets available to the computing systems at the analytical infrastructure. In these implementations, the user may have the ability to identify the intersection of investigators from the organization's internal data set and the health records data received at the analytical infrastructure.

In some implementations, the user may select an investigator from the list of ranked investigators and select to view the diagnosis details for the investigator. The computing systems at the analytical infrastructure may generate a diagnosis bar chart that displays the number of patients diagnosed with the user selected diagnosis each month. The user may have the ability to select to display the diagnoses based on the age of the patient diagnosed. The data may be displayed for a user selected time period. For example the user may select to have the data displayed for the last year, or last two years. The diagnosis chart may also break down the diagnoses based on the gender of the patient.

Figure 9:
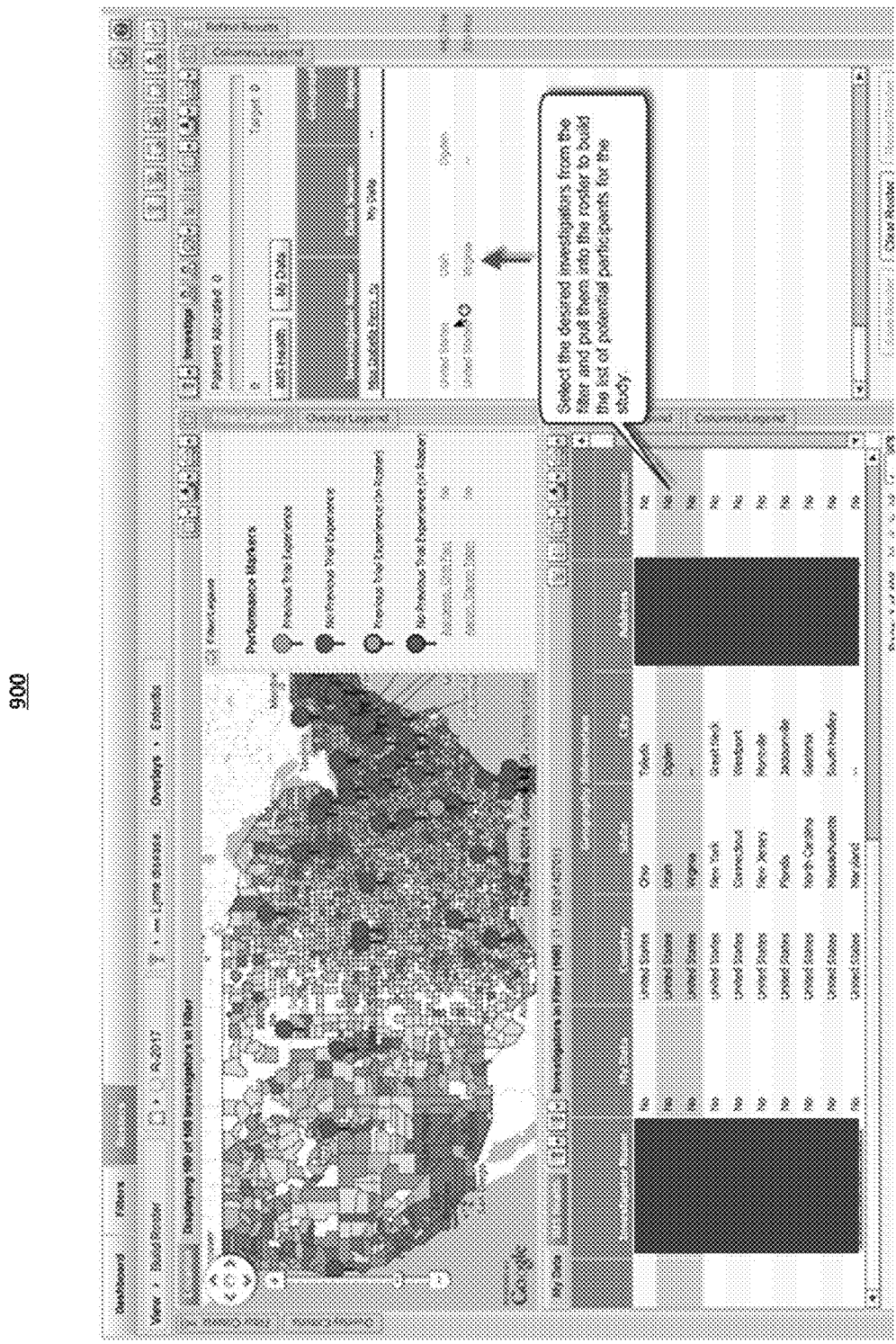

FIG. 9 illustrates an example user interface 900 that may be displayed when a user of the performance indicator offering selects to create a roster. The roster may be used to list the investigators selected by the user to participate in a clinical trial. The user may select the desired investigators from the list of ranked investigators into the roster drop down to build the list of potential participants for the clinical trial study. In some implementations, when the user adds an investigator to the roster the investigator is identified on the map by a marker. In some implementations, the computing systems at the analytical infrastructure may automatically generate a roster of investigators by selecting the top ranked investigators. In some implementations, when a user selects to have investigators ranked by a particular key performance indicator, the computing systems at the analytical infrastructure may generate a roster based on all investigators that records include data related to the particular performance indicator. In some implementations, the computing systems at the analytical infrastructure may communicate with the computing systems associated with investigators. In these implementations, when an investigator is placed in the roaster of investigators, the computing systems at the analytical infrastructure may communicate the inclusion in the roster to the investigator.

Figure 10:
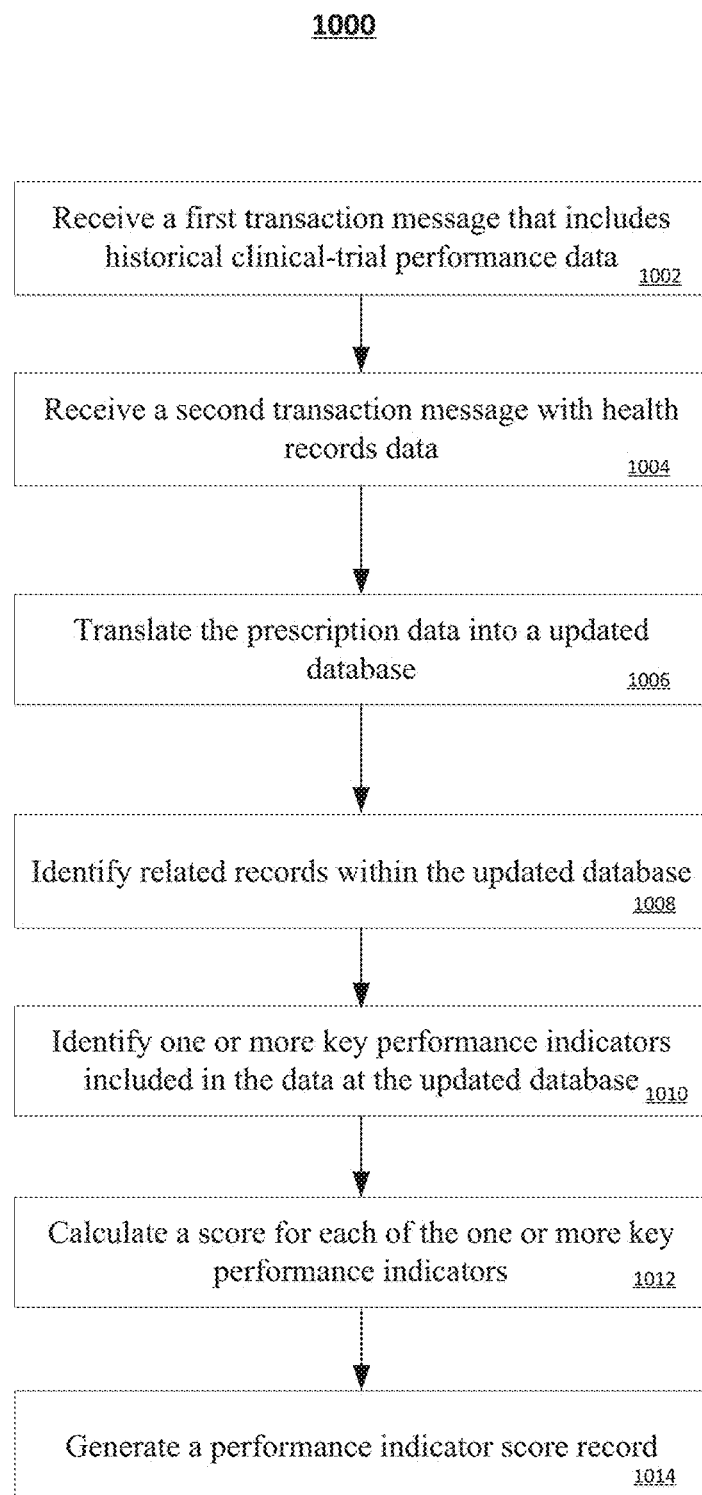
FIG. 10 is a flow chart of an example process for generating a performance indicator score record.

FIG. 10 is a flow chart of the process for generating a performance indicator score record. The computing systems at the analytical infrastructure receive a first transaction message that includes historical clinical trial performance data from one or more processors at a clinical research organization (1002). The received data file may be stored at a one or more databases at the computing systems at the analytical infrastructure. The transaction message received may be a data file, a stream of data, or a datagram. The historical clinical trial performance data may be data collected and maintained by one or more processors at a clinical research organization. The historical data may include detailed data of clinical trial studies carried out in the past by the clinical research organization. The historical clinical trial performance data may include the number of patients that participated in a clinical trial, the start date of the clinical trial, the completion date of the clinical trial, the number of days a physician took to response to a query, and any other suitable historical clinical trial data collected. The historical clinical trial data may be communicated to the computing systems at the analytical infrastructure on a periodical basis. For example, the historical data may be received at the computing systems of the analytical infrastructure every week, once a month, or quarterly. The historical data may be received at the computing systems of the analytical infrastructure at any suitable period. In some implementations, the one or more processors at the clinical research organization may communicate the historical data to the computing systems on a daily basis.

The computing systems at the analytical infrastructure receive a second transaction message with health records data indicative of insurance claims data (1004). The transaction message received may be a data file, a stream of data, or a datagram. The received health records data may be stored at a one or more databases at the computing systems of the analytical infrastructure. The health records data received may include health insurance claims from a larger percentage of pharmacies across the United States of America. The health insurance data me be part of IMS health data. The IMS health data may include patient data, prescriber data, and health insurance claims data that represents a large percentage of global health care data. The health records data may include medical details for patients. The health records data may be anonymized data yet may be rich in details of gender, sex, age, diagnosis, and any other suitable patient details. The computing systems at the analytical infrastructure may receive health records data from one or more processors associated with one or more hospitals, treatment facilities, prescribing facilities, Integrated Delivery Networks (IDNs), one or more patient systems, one or more prescriber systems, and one or more payer systems.

The computing systems at the analytical infrastructure may translate the health records data and the received historical clinical trial performance data into an updated database based on the received historical clinical trial performance data (1006). The health records data received may be stored at one or more databases at the computing systems at the analytical infrastructure. The received historical clinical trial performance data may be stored at the one or more databases. The two data sources may be combined logically across databases or physically within the same database to form a universal data set that integrates the data sources. The integrated data sources may be stored as one or more updated databases. The updated database may be an extension to the one or more databases that store the health records data and/or the clinical trial data. The updated database may be a computational database. The updated database may have the processing capability to execute extensive computations and calculations. The updated database may perform extensive calculations and computations on the health records data and the clinical trial historical data sources at the updated database high processing speeds. The updated database may be an energy efficient and time efficient database. The updated database may process large amounts of clinical trial historical data and health records data at very high speeds. The updated database may have the processing ability to allow the calculations and computations carried out on the data sources at the updated database to be quick and effective. The computing systems at the analytical infrastructure may identify related record within the updated database (1008). Data associated with a particular investigator or physician may be identified in the data sources and tagged with an identifier. Data associated with a particular geographical area, diagnosis, or physician specialty may be identified in the data sources and tagged with an identifier.

The computing systems at the analytical infrastructure may identify one or more key performance indicators in the updated database (1010). The data processing module at the computing systems may field and/or mine the universal data for data that may be used as a key performance indicator. For example, the data processing module may identify clinical trial data that may have recently been received at the computing systems, with dates that align with the current dates, and may identify the data as belonging to a currently active study. The computing systems at the analytical infrastructure may identity currently active clinical trial studies as an active studies key performance indicator. The data processing module may identify data for related records with one or more key performance indicators. The related records may be related by diagnosis, geographical location, investigator or physician, or any other suitable relation. For example, for a particular investigator, which may be identified with an investigator tag, the data processing module may identify the time between the date when the final protocol was approved and the date the site initiated to identify the final protocol approved to site initiation key performance indicator.

The computing systems at the analytical infrastructure may calculate a score for each of the one or more key performance indicators (1012). The administrative user at the computing systems at the analytical infrastructure may establish a medium performance range for each identified key performance indicator. The data received and identified for each key performance indicator may then be compared, by the statistical analysis module, to the medium performance range established by the administrative user. In some implementations, the administrative user may indicate the start and end points of the medium performance range for each identified key performance indicator. In other implementations, the administrative user may enter two values to indicate the start and end points of the medium performance range in terms of percentiles. In these implementations, the administrative user provides a ranking that is relative to other investigators. In some implementations, the performance indicator offering may be adapted to allow an end user to establish a medium performance range for each key performance indicator. The statistical analysis module at the computing systems may assign a score to the key performance indicators. In some implementations, the score assigned to the one or more identified key performance indicators may be a high score of 3, a medium score of 2, or low score of 1. In some other implementations, any other suitable score range may be used.

The computing systems at the analytical infrastructure may generate a performance indicator score record (1014). In some implementations, the administrative user may determine which of the one or more key performance indicators may be used to assess the performance of an investigator. In some implementations, the end user may have the ability to identify which key performance indicators should be used to generate the performance indicator score record for a particular investigator. The end user may select that the performance indicator score record be generated based on one key performance indicator. For example, the end user may select to have the performance indicator score based on the score assigned to the total studies key performance indicator. In these examples, the computing systems at the analytical infrastructure may generate a performance indicator score record, and rank one or more physicians based on the total studies key performance indicator, that is the number of clinical trial studies the physician has participated. In some implementations, the end user may select that the performance indicator score record be generated based on one or more key performance indicators. In these implementations, the end user may have the ability to identify the one or more key performance indicators that should be used to generate the performance indicator score record. The computing systems at the analytical infrastructure may generate the performance indicator score record for a particular investigator based on a weighted average of the one or more identified key performance indicators. The weight to each of the one or more key performance indicators may be assigned by the administrative user. In other implementations, the weight to each of the one or more key performance indicators may be assigned by the end user. In some implementations, the computing systems at the analytical infrastructure may generate a performance indicator score record for a particular investigator based on an algorithm. In some implementations, the end user may select which key performance indicators should be included in the calculation of the performance indicator score record for a particular investigator, or group of one or more investigators.

In some implementations, the performance indicator score record may be based on a therapeutic area. In these implementations, the weight of a particular key performance indicator may be evaluated differently based on the therapeutic area. For example, a clinical trial organization may decide that in a Respiratory clinical trial study, a monthly screening rate of fifteen or more patients is considered a high performance, whereas in an Oncology clinical trial study, a screening rate of five or more patients is considered a high performance. In some implementations, the end user may select to determine the performance indicator score for one or more investigators based on one key performance indicator. In these implementations, the computing systems at the analytical infrastructure may present the score of the selected key performance indicator as the performance indicator score record for the investigator.

The computing systems at the analytical infrastructure may rank one or more investigators/physicians based on the generated performance indicator score. The computing systems at the analytical infrastructure may rank one or more physicians based on the user selected key performance indicators and may generate a ranked list. The ranked list of investigators may be displayed to the user through the performance indicator tool application. In some implementations, the one or more investigators may be ranked based on a performance indicator score generated from the evaluation of one key performance indicator. In these implementations, the end user may select a single key performance indicator that the one or more investigators should be ranked according to. In some other implementations, the one or more investigators may be ranked based on a performance indicator score generated from the evaluation of one or more key performance indicators. In these implementations, each of the one or more key performance indicators may be assigned a weight and the performance indicator score may be generated based on the weighted average of the one or more key performance indicators evaluated. The performance indicator score may be generated based on an algorithm that includes the one or more key performance indicators. In some implementations, the user may select to rank the investigators both on the overall performance indicator score and the score for one or more key performance indicators.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method comprising:
receiving, by one or more processors and from a first database system of a clinical research organization, a first transaction message that includes historical clinical trial performance data for clinical trials conducted by a first physician, wherein historical clinical trial performance data specifies an initiation date and a screening date for each patient associated with the clinical trials conducted by the first physician;
receiving, by the one or more processors and from a set of second database systems other than the first database system, a second transaction message that includes health records data for the clinical trials conducted by the first physician, wherein the health records data specifies a number of patients that were screened by the first physician and a total number of patients enrolled in the clinical trials conducted by the first physician;
removing, by the one or more processors and from the first and second transaction messages, nominative data representing identifiable information for a first set of patients associated with the historical clinical trial performance data and a second set of patients associated with the health records data;
generating, by the one or more processors, a first de-identified transaction message and a second de-identified transaction message based on removing the nominative data from the first and second transaction messages;
identifying, by the one or more processors, a first key performance indicator associated with the historical clinical trial performance data, wherein the first key performance indicator represents an average time period for a particular physician to examine a particular set of patients within one or more clinical trials;
identifying, by the one or more processors, a second key performance indicator associated with the health records data, wherein the second key performance indicator represents a number of patients that have been screened by a particular physician within one or more clinical trials;
generating, by the one or more processors and within a longitudinal database, a first identifier mapping a first portion of the first de-identified transaction message and a first portion of the second de-identified transaction message, the first portions of the first and second de-identified transaction messages corresponding to data descriptive of the first key performance indicator;
generating, by the one or more processors and within the longitudinal database, a second identifier mapping a second, different portion of the first de-identified transaction message and a second, different portion of the second de-identified transaction message, the second portions of the first and second de-identified transaction messages corresponding to data descriptive of the second key performance indicator;
storing, by the one or more processors and within the longitudinal database, an aggregate performance transaction record for the first physician, wherein:
the aggregate performance transaction record includes the first de-identified transaction message, the second de-identified transaction message, the first identifier and the second identifier, and
the aggregate performance transaction record enables the one or more processors to perform one or more computations on data of the first physician included within the aggregate performance transaction record in a first time period that is shorter than a second time period for performing the one or more computations on data of the first physician stored within the first database system and the set of second database systems but not stored within the aggregate performance transaction record;
computing, by the one or more processors, a first performance score for the first key performance indicator, wherein:
the first performance score represents a patient screening milestone achievement by the first physician for examining the first set of patients, and
the first performance score is computed based on:
the first identifier,
the initiation dates for the patients associated with the clinical trials conducted by the first physician, and the screening dates for the patients associated with the clinical trials conducted by the first physician;

computing, by the one or more processors, a second performance score for the second key performance indicator, wherein:

the second performance score represents a screening throughput of the first physician within the clinical trials, and the second performance score is computed based on:
the second identifier,
the number of patients that were screened by the first physician, and
the total number of patients enrolled in the clinical trials conducted by the first physician;

obtaining, by the one or more processors, data indicating a first weight and a second weight corresponding to respective prioritizations of the first and second key performance indicators;

computing, by the one or more processors, an overall performance score for the first physician based on combining the first and second performance scores according to the first and second weights; and providing, by the one or more processors, data indicating the overall performance score for the first physician.

2. The computer-implemented method of claim 1, wherein the second transaction message comprises health records data indicative of patient data and prescriber data associated with the one or more database systems other than the system of the clinical research organization.

3. The computer-implemented method of claim 1, wherein the first and second weights are assigned respectively to the first and second key performance indicators based on user input submitted by an administrative user associated with a client device, the user input specifying the respective prioritizations according to therapeutic areas corresponding to each of the first and second key performance indicators.

4. The computer-implemented method of claim 3, further comprising:

receiving, by the one or more processors and from the client device, data indicating a request for the overall performance score for the first physician, the request identifying the respective prioritizations for the first and second key performance indicators;

wherein the data indicating the overall performance score for the first physician is provided for output in response to receiving the request for the overall performance score; and wherein the overall performance score is provided for output on a user interface presented through which the user provides the user input.

5. The computer-implemented method of claim 1, further comprising:

generating, by the one or more processors, an aggregate performance transaction record for a second physician based on the first transaction message and the second transaction message;

computing, by the one or more processors, a first performance score for the second physician corresponding to the first key performance indicator;

computing, by the one or more processors, a second performance score for the second physician corresponding to the second key indicator; and computing, by the one or more processors, an overall performance score for the second physician based on combining the first and second performance scores for the second physician according to the first and second weights.

6. The computer-implemented method of claim 5, further comprising:

computing, by the one or more processors, a first rank score for the first physician based on the overall performance score computed for the first physician;

computing, by the one or more processors, a second rank score for the second physician based on the overall performance score computed for the second physician; and providing, by the one or more processors and for output to a client device, data indicating the computed first rank score for the first physician and the computed second rank score for the second physician.

7. The computer-implemented method of claim 6, wherein providing the data indicating the computed respective ranks for the first physician and the second physician comprises providing data indicating a ranked list based on values of the respective rank scores computed for the first physician and the second physician.

8. The computer-implemented method of claim 1, wherein the first transaction message comprises historical clinical-trial performance stored within at least one of a data file, a stream of data or a datagram.

9. A system comprising:

one or more computers and one or more storage devices storing instructions that are operable, when executed by one or more computers, to cause the one or more computers to perform operations comprising:

receiving, by one or more processors and from a first database system of a clinical research organization, a first transaction message that includes historical clinical trial performance data for clinical trials conducted by a first physician, wherein historical clinical trial performance data specifies an initiation date and a screening date for each patient associated with the clinical trials conducted by the first physician;

receiving, by the one or more processors and from a set of second database systems other than the first database system, a second transaction message that includes health records data for the clinical trials conducted by the first physician, wherein the health records data specifies a number of patients that were screened by the first physician and a total number of patients enrolled in the clinical trials conducted by the first physician;

removing, by the one or more processors and from the first and second transaction messages, nominative data representing identifiable information for a first set of patients associated with the historical clinical trial performance data and a second set of patients associated with the health records data;

generating, by the one or more processors, a first de-identified transaction message and a second de-identified transaction message based on removing the nominative data from the first and second transaction messages;

identifying, by the one or more processors, a first key performance indicator associated with the historical clinical trial performance data, wherein the first key performance indicator represents an average time period for a particular physician to examine a particular set of patients within one or more clinical trials;

identifying, by the one or more processors, a second key performance indicator associated with the health records data, wherein the second key performance indicator represents a number of patients that have been screened by a particular physician within one or more clinical trials;

generating, by the one or more processors and within a longitudinal database, a first identifier mapping a first portion of the first de-identified transaction message and a first portion of the second de-identified transaction message, the first portions of the first and second de-identified transaction messages corresponding to data descriptive of the first key performance indicator;

generating, by the one or more processors and within the longitudinal database, a second identifier mapping a second, different portion of the first de-identified transaction message and a second, different portion of the second de-identified transaction message, the second portions of the first and second de-identified transaction messages corresponding to data descriptive of the second key performance indicator;

storing, by the one or more processors and within the longitudinal database, an aggregate performance transaction record for the first physician, wherein:
the aggregate performance transaction record includes the first de-identified transaction message, the second de-identified transaction message, the first identifier and the second identifier, and
the aggregate performance transaction record enables the one or more processors to perform one or more computations on data of the first physician included within the aggregate performance transaction record in a first time period that is shorter than a second time period for performing the one or more computations on data of the first physician stored within the first database system and the set of second database systems but not stored within the aggregate performance transaction record;

computing, by the one or more processors, a first performance score for the first key performance indicator, wherein:
the first performance score represents a patient screening milestone achievement by the first physician for examining the first set of patients, and
the first performance score is computed based on:
the first identifier,
the initiation dates for the patients associated with the clinical trials conducted by the first physician, and
the screening dates for the patients associated with the clinical trials conducted by the first physician;

computing, by the one or more processors, a second performance score for the second key performance indicator, wherein:
the second performance score represents a screening throughput of the first physician within the clinical trials, and
the second performance score is computed based on:
the second identifier,
the number of patients that were screened by the first physician, and
the total number of patients enrolled in the clinical trials conducted by the first physician;

obtaining, by the one or more processors, data indicating a first weight and a second weight corresponding to respective prioritizations of the first and second key performance indicators;

computing, by the one or more processors, an overall performance score for the first physician based on combining the first and second performance scores according to the first and second weights; and providing, by the one or more processors, data indicating the overall performance score for the first physician.

10. The system of claim 9 wherein the second transaction message comprises health records data indicative of patient data and prescriber data associated with the one or more database systems other than the system of the clinical research organization.

11. The system of claim 9, wherein the first and second weights are assigned respectively to the first and second key performance indicators based on user input submitted by an administrative user associated with a client device, the user input specifying the respective prioritizations according to therapeutic areas corresponding to each of the first and second key performance indicators.

12. The system of claim 9, wherein the operations further comprise:
generating, by the one or more processors, an aggregate performance transaction record for a second physician based on the first transaction message and the second transaction message;
computing, by the one or more processors, a first performance score for the second physician corresponding to the first key performance indicator;
computing, by the one or more processors, a second performance score for the second physician corresponding to the second key indicator; and
computing, by the one or more processors, an overall performance score for the second physician based on combining the first and second performance scores for the second physician according to the first and second weights.

13. A non-transitory computer-readable medium storing software comprising instructions executable by one or more which, upon such execution, cause the one or more computers to perform operations comprising:
receiving, by one or more processors and from a first database system of a clinical research organization, a first transaction message that includes historical clinical trial performance data for clinical trials conducted by a first physician, wherein historical clinical trial performance data specifies an initiation date and a screening date for each patient associated with the clinical trials conducted by the first physician;
receiving, by the one or more processors and from a set of second database systems other than the first database system, a second transaction message that includes health records data for the clinical trials conducted by the first physician, wherein the health records data specifies a number of patients that were screened by the first physician and a total number of patients enrolled in the clinical trials conducted by the first physician;
removing, by the one or more processors and from the first and second transaction messages, nominative data representing identifiable information for a first set of patients associated with the historical clinical trial performance data and a second set of patients associated with the health records data;
generating, by the one or more processors, a first de-identified transaction message and a second de-identified transaction message based on removing the nominative data from the first and second transaction messages;
identifying, by the one or more processors, a first key performance indicator associated with the historical clinical trial performance data, wherein the first key performance indicator represents an average time period for a particular physician to examine a particular set of patients within one or more clinical trials;

identifying, by the one or more processors, a second key performance indicator associated with the health records data, wherein the second key performance indicator represents a number of patients that have been screened by a particular physician within one or more clinical trials;

generating, by the one or more processors and within a longitudinal database, a first identifier mapping a first portion of the first de-identified transaction message and a first portion of the second de-identified transaction message, the first portions of the first and second de-identified transaction messages corresponding to data descriptive of the first key performance indicator;

generating, by the one or more processors and within the longitudinal database, a second identifier mapping a second, different portion of the first de-identified transaction message and a second, different portion of the second de-identified transaction message, the second portions of the first and second de-identified transaction messages corresponding to data descriptive of the second key performance indicator;

storing, by the one or more processors and within the longitudinal database, an aggregate performance transaction record for the first physician, wherein:
the aggregate performance transaction record includes the first de-identified transaction message, the second de-identified transaction message, the first identifier and the second identifier, and
the aggregate performance transaction record enables the one or more processors to perform one or more computations on data of the first physician included within the aggregate performance transaction record in a first time period that is shorter than a second time period for performing the one or more computations on data of the first physician stored within the first database system and the set of second database systems but not stored within the aggregate performance transaction record;

computing, by the one or more processors, a first performance score for the first key performance indicator, wherein:
the first performance score represents a patient screening milestone achievement by the first physician for examining the first set of patients, and
the first performance score is computed based on:
the first identifier,
the initiation dates for the patients associated with the clinical trials conducted by the first physician, and
the screening dates for the patients associated with the clinical trials conducted by the first physician;

computing, by the one or more processors the second identifier, a second performance score for the second key performance indicator, wherein:
the second performance score represents a screening throughput of the first physician within the clinical trials, and
the second performance score is computed based on:
the second identifier,
the number of patients that were screened by the first physician, and
the total number of patients enrolled in the clinical trials conducted by the first physician;

obtaining, by the one or more processors, data indicating a first weight and a second weight corresponding to respective prioritizations of the first and second key performance indicators;

computing, by the one or more processors, an overall performance score for the first physician based on combining the first and second performance scores according to the first and second weights; and providing, by the one or more processors, data indicating the overall performance score for the first physician.

* * * * *